United States Patent [19]

Laborit

[11] 4,169,158

[45] Sep. 25, 1979

[54] PYRIDAZINE DERIVATIVES IN ALLEVIATING DEPRESSIVE STATES

[75] Inventor: Henri Laborit, Paris, France

[73] Assignee: Centre d'Etudes Experimentales et Cliniques de Physio Biologie de Pharmacologie et d'Eutonologie, Paris, France

[21] Appl. No.: 820,489

[22] Filed: Jul. 29, 1977

Related U.S. Application Data

[60] Continuation of Ser. No. 450,589, Mar. 13, 1974, abandoned, which is a division of Ser. No. 260,096, Jun. 6, 1972, abandoned.

[30] Foreign Application Priority Data

Jun. 18, 1971 [GB] United Kingdom ............... 28737/71

[51] Int. Cl.$^2$ ............................................. A61K 27/00
[52] U.S. Cl. .................................................. 424/248.56
[58] Field of Search ..................................... 424/248.56

[56] References Cited

PUBLICATIONS

Ornellas, Biochemistry & Pharmacology, vol. 20, pp. 2141–2147.
Laborit et al., Agressologie, (1969), 10(10), pp. 469–478.
Conn, Current Therapy, (1970), pp. 671–677.
Ornellas, M. R. et al., Agressologie, 10:437–449, (1969).
Thuret, F. et al., Agressologie, 11:417–420, (1970).

*Primary Examiner*—Stanley J. Friedman
*Attorney, Agent, or Firm*—Bacon & Thomas

[57] ABSTRACT

A class of pyridazine derivatives useful as antidepressants and mood elevators when used in medicine of the formula:

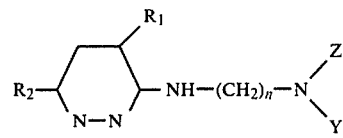

wherein
$R_1$ is a hydrogen atom or a lower alkyl group;
$R_2$ is an aryl group such as phenyl or naphthyl or substituted phenyl and N is 2 or 3.
Y and Z may be the same or different lower alkyl groups or taken together with the nitrogen atom form a heterocyclic ring wherein Z and Y are lower alkylene radicals cyclized in a ring which contains an oxygen atom linked between them and the other ends of the alkylene chain link to the nitrogen atom. The invention also includes nontoxic acid addition salts thereof suitable for pharmaceutical use and methods for their administration and use as therapeutic agents for humans.

4 Claims, No Drawings

PYRIDAZINE DERIVATIVES IN ALLEVIATING DEPRESSIVE STATES

This is a continuation of application Ser. No. 450,589 filed on Mar. 13, 1974 which is a division of Ser. No. 260,096 filed June 6, 1972, both are abandoned.

BRIEF STATEMENT OF THE INVENTION

This invention relates to a group of pyridazine derivatives useful as therapeutic agents, particulrly as antidepressant agents in medicine.

The compounds which comprise the composition aspect of the invention are 3-aminoalkylamino-4-alkyl-6-aryl-pyridazines of the formula:

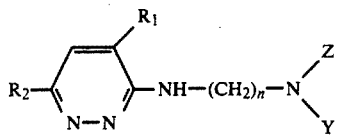

wherein
$R_1$ is a hydrogen atom or a lower alkyl group;
$R_2$ is an aryl or substituted aryl group;
n is 2 or 3; and
Y and Z may be the same or different lower alkyl groups, or

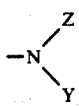

is a heterocyclic radical wherein Z and Y are lower alkylene groups cyclized to form a ring which contains an oxygen atom linked between the alkylene groups and the nitrogen atom attached to the opposite end of each alkylene group.

In formula (I), the lower alkyl groups may suitably contain from 1 to 3 carbon atoms, and the lower alkylene groups, 2 carbons each; and when $R_1$ is a lower alkyl group, it is preferably a methyl group. Group $R_2$ may be a phenyl, substituted phenyl or naphthyl group. When

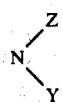

is a heterocyclic radical, it may suitably be a morpholino, piperidino or pyrrolidino group.

The invention also includes the acid addition salts of the compounds of formula (I) formed by reaction of the base with a suitable organic or inorganic acid such as tartaric acid or hydrochloric acid to name two well known representative acids of this group.

Within the broader group of compounds their is one compound which has particular outstanding human utility as an antidepressant. Its formula is as follows:

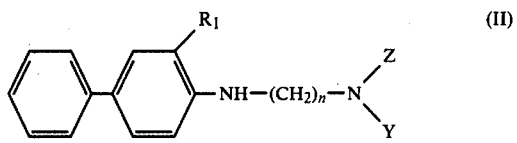

in which R is a methyl group, n is 2 and Z and Y are cyclyed to form a morpholino group of the structure

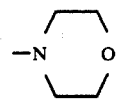

and especially the dichloride salt of this base. The preparation of this compound is illustrated in the following general reaction scheme set forth to show the reaction of a chloropyridazine and an amine according to the following outline. In the case of formation of compound I above the particular chloropyridazine reactant employed would have Ar represent a phenyl group and $R_1$ methyl group. The amine reactant in this particular case would be one where n is 2 and Z and Y are cyclyed to form with N- a morpholino ring. In the formation of the other members of the series Ar, $R_1$, n, Y and Z would have the meanings set forth in the general definition given above.

In the general manner of preparation of all of the compounds of the series described above an inert organic solvent such as butanol is employed at the boiling point of the solvent and in the presence of small amounts of metallic copper which acts as a catalyst.

The following Table I sets forth eight compounds which fall within the scope of the invention and tabulates the functional groups appearing in each as represented in the general formula (I) above:

Table 1

| Compound No. | $R_1$ | $R_2$ | n | $N<^Z_Y$ | Salt | Melting Point (°C.) |
|---|---|---|---|---|---|---|
| 1 | $CH_3$ | $C_6H_5$ | 2 | N O (morpholino) | Dihydrochloride | 182 |
| 2 | $CH_3$ | $C_6H_5$ | 3 | N O (morpholino) | Dihydrochloride | 196 |

Table 1-continued

| Compound No. | $R_1$ | $R_2$ | n | $N{<}^Z_Y$ | Salt | Melting Point (°C.) |
|---|---|---|---|---|---|---|
| 3 | $CH_3$ | naphthyl | 2 | morpholino | Dihydrochloride | 215 |
| 4 | $CH_3$ | $C_6H_5$ | 2 | $N(C_2H_5)_2$ | Dihydrochloride | 96 |
| 5 | $CH_3$ | $C_6H_5$ | 2 | $N(C_2H_5)_2$ | Tartrate | 168 |
| 6 | H | $C_6H_5$ | 2 | morpholino | Dihydrochloride | 232 |
| 7 | $CH_3$ | $p$-$CH_3O$—$C_6H_4$ | 2 | morpholino | Dihydrochloride | 225 |
| 8 | $C_2H_5$ | $C_6H_5$ | 2 | morpholino | Dihydrochloride $H_2O$ | 172 |

In the preceding table the compound noted as No. 1 wherein $R_1$ is methyl and $R_2$ is phenyl ring with the value for n being 2 and the amino function being amorpholino group is the preferred member of this series for which a considerable amount of human clinical data has been amassed in support of the rather unique anti-depressant activity of this compound; and its 7 other related analogs as precisely identified in the table. All of these compounds have been made and tested in animals to the extent that their utility as anti-depressants has been established.

The following examples illustrate the specific modes of preparation of the eight compounds enumerated in the preceding table.

EXAMPLE 1

Synthesis of morpholinoethyl-3-methyl-4-phenyl-6-pyridazine dihydrochloride (Compound No. 1).

(a) Formation of the free base

Heat by reflux for twelve hours a mixture of 0.1 mole (20.4 g) of chloro-3-methyl-4-phenyl-6-pyridazine, of 0.2 mole (26.2 g) of N-(2-aminoethyl)-morpholine in 100 ml of n-butanol and in presence of a small amount of powdered copper.

After this operation, pour the hot solution into 250 ml of cold water. Filter the solution obtained on sintered glass, wash the precipitate with ether. Place the filtrate and the ether washings in a beaker. Extract with either (2×150 ml). Then extract the ethereal phase with $H_2SO_4N$ (roughly 250 ml). Then alkalinize the acid solution with a 10% solution of sodium carbonate. Let stand for one night to obtain crystallization.

Filter the solution, and fine buff-colored meedles are obtained which are recrystallized in isopropanol. Yield is 15 g, or 53%.

(b) Formation of the hydrochloride

Dissolve the base obtained in a small amount of anhydrous acetone. Add twice the volume of anhydrous ether and make a flow of gaseous HCl pass through. Recrystallization of the hydrochloride is performed in dehydrated alcohol.

The yield after recrystallization is 17 g, or 90%.

EXAMPLE 2

Synthesis of morpholinopropylamino-3methyl-4-phenyl-6-pyridazine dihydrochloride (Compound No. 2).

Proceed as in Example 1, with 20.4 g (0.1 mole) of chloro-3-methyl-4-phenyl-6-pyridazine and of 28.9 g (0.2 mole) of N-(3-aminopropyl)-morpholine, with which 15 g of base in the form of buff-colored needles are obtained, in other words 40% of the compound. Yield in hydrochloride: 16 g, or 86%.

EXAMPLE 3

Synthesis of (morpholinoethylamino-3) methyl-4 (2-naphtyl)-6-pyridazine dihydrochloride (Compound No. 3).

Proceed as in Example 1, at the start with 25.4 g (0.1 mole) of chloro-3-methyl-4-naphtyl-6 pyridazine and with 26.2 g (0.2 mole) of N-(2-aminoethyl)-morpholine, and 14 g of base are obtained, in form of needles, which is a yield of 40%.

Yield in hydrochloride: 8 g, namely 48%.

EXAMPLE 4

Synthesis of (beta-diethylaminoethylamino)-3methyl-4-phenyl-6-pyridazine dihydrochloride (Compound No. 4)

Proceed as in Example 1, at the start with 22.5 g (0.11 mole) of chloro-3-methyl-4-phenyl-6-pyridazine and with 25.6 g (0.22 mole) of diethylaminoethylamine, and 14 g of liquid base, which is a 45% yield.

Yield in hydrochloride: 13 g, or 74%.

EXAMPLE 5

Synthesis of (beta-dimethylaminoethylamino) 3 methyl-4-phenyl-6-pyridazine tartrate (Compound No. 5).

Proceed as in Example 1; at the start with 24.6 g (0.12 mole) of chloro-3-methyl-4-phenyl-6-pyridazine and with 21.2 g (0.24 mole) of dimethylaminoethylamine, 8 g of liquid base are obtained, which is a yield of 26%.

Yield in tartrate: 7 g, or 55%.

EXAMPLE 6

Synthesis of (morpholinoethylamino) 3-phenyl-6 pyridazine dihydrochloride (Compound No. 6).

Proceed as in Example 1; at the start with 10 g (0.05 mole) of chloro-3-phenyl-6-pyridazine and with 13 g (0.1 mole) of N(2-aminoethyl)morpholine, 13.5 g of crystallized base are obtained, which is a yield of 94%.

Yield in hydrochloride: 14 g, namely 83%.

EXAMPLE 7

Synthesis of (morpholinoethylamino)-3-methyl-4-(paramethoxyphenyl)-6-pyridazine dihydrochloride (Compound No. 7).

Proceed as in Example 1; start with 17.4 g (0.074 mole) of chloro-3-methyl-4-(p-methoxy)-phenyl-6 pyridazine and with 19.8 g (0.15 mole) of N-(2 aminoethyl)-morpholine: 11 g of liquid base are obtained, which is a yield of 47%.

Yield in hydrochloride: 6 g, or 43%.

EXAMPLE 8

Synthesis of (morpholinoethylamino)-3-ethyl-4-phenyl-6-pyridazine dihydrochloride (Compound No. 8).

Proceed as in Example 1: start with 21.8 g (0.1 mole) of chloro-3-ethyl-4-phenyl-6-pyridazine and with 26.2 g (0.2 mole) of N(2-aminoethylmorpholine), 15 g of base are obtained, which is a yield of 48%.

Yield in hydrochloride: 12 g, or 67%.

The compounds of the invention are pharmacologically active substances which exhibit psychotropic properties, especially as antidepressants. Accordingly, the compounds of the invention may be formulated with pharmaceutical carriers and diluents in the conventional ways, to provide pharmaceutical compositions, and may be administered by the conventional routes used for administering anti-depressants.

The dosage range for such agents may vary with the weight of the subject to which the same is administered. However, the range of 0.17 mg. to 2.2 mg. per day per kilogram of body weight of the patient by oral administration of tablets of 50 mgs. each may be noted. These amounts may be administered in concert with such conventional diluents in either liquid or solid form. If tablets are the form of oral administration, then the carrier may be lactose or starch or several of such well known agents for administration of the active ingredients.

Experimental and clinical studies on the compounds of the invention such as compound 1 for example, indicate that their metabolic behavior and pharmacological activity differ markedly from those of previously known pyridazine anti-depressants when compared thereto. These known pyridazine anti-depressants are generally of the formula:

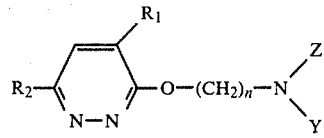

wherein $R_1$, $R_2$, n, Y and Z have the meanings already given above.

For example, it is found that Compound No. 1 of Table I above increases oxygen consumption in tissue sections while reducing glucose utilization and lactic acid formation. Adding this same drug in vitro to sections derived from pretreated animals shows such results. However with homogenates the glucose utilization and lactic acid formations are increased instead of being reduced. This indicates a general metabolic activation triggered conceivably at the level of the cell membrane. This becomes more clear during chronic or long term administration of the drug since this results in a decrease both of cerebral glycogen and glucose. However, the marked decrease of hexokinase activity seems to show that it is from glycogen that the feeding of metabolic pathways is performed. The increase in activity of G 6-P dehydrogenase suggests that the beneficiaries are the pentose pathways. The decrease of the formation of lactic acid, despite the activity of LDH, indicates that the pyruvate is completely utilized by the tricarboxylic cycle. This is confirmed by the fact that without any increase of ATPase activity one can observe a marked increase in the concentration of ATP, and a decrease of inorganic phosphorous accompanying the consumption of $O_2$. There is therefore an increase in the activity of oxidative phosphorylations. However, in acute administration, there also can be observed an increase of glycolysis. The stability of brain calcium levels is perhaps nothing more than the sign of an increased calcium turnover.

Furthermore, considered its lack of action on the liver and brain monoamineoxydase, it is possible to conclude that its effectiveness is due to a complex effect of central excitation which with high doses, can develop into an epileptic episode accompanied by stimulation of the striatum and in particular of the caudate nucleus. The increase in excitability of the Median Center suggests an increase in the processes of attention and focalization. Its effect on the limbic system is that of an antineurotic, not that of an antipsychotic with a decrease of the intensity and of the duration of the postdischarges. The slight decrease of the excitability of the associated reticular formation, suggests tranquilizing and antianxiety properties.

The functional spontaneous depression of the caudate nucleus suggests its usefulness in the treatment of extrapyramidal syndromes, since the drug seems to act in a similar way to L-dopa, that is to say by inhibition, while decreasing the threshold of excitability.

Inhibition of the anterior hypothalamus, as opposed to stimulation of the posterior hypothalamus by the drug would appear to justify the study of its effect on endocrine balance.

But of greater significance is the increased hypertensive response to direct excitation of the posterior hypothalamus, response which is absent following excitation of the sciatic nerve.

This finding would seem to justify the inference that there is a pharmacological depression of the multisynaptic pathyways connecting the posterior thalamus to peripheral receptors. These findings imply also a powerful analgesic effect which confirms the higher level of central and behavioral reactions when the sciatic nerve is excited.

It can therefore be concluded that Compound No. 1 and particularly those defined in the group under formula No. 1 are antidepressants of a new type.

The characteristics of this new compound may be summed up as follows:

1. It does not appear to act directly, as do other antidepressants, on catecholamine metabolism. In particular it is not an MAO inhibitor.

2. It also has antineurotic characteristics depressant of the limbic system and of excitation of the reticular formations originating in peripheral receptors.

3. It could increase the capacity to concentrate, by its stimulant effect on the intralaminar nuclei of the thalamus.

4. Its CNS stimulating effect seems also linked to its inhibitory effect on the anterior hypothalamus and its stimulating effect on the posterior hypothalamus.

These neurophysiological properties correspond to the biological mechanisms of the compound.

1. It is a stimulator of non-decoupling oxydative metabolisms (increase of ATP synthesis and decrease of inorganic phosphate, increase in $O_2$ consumption)

2. But these properties seem to be secondary to a membrane-type of action, similar that of ouabain which could conceivably be an inhibition of $Na^+K^+$ AtPase (study in process) acting on metabolism through the medium of ionic exchanges through the membrane and a secondary activation of the $Na^+$ pump.

3. Increased cerebral protein synthesis produced by the one found would appear of paramount importance; conceivably it is secondary to the increase in metabolic activity. It is well known that it is essential for long term memory which could conceivably be improved as could learning.

4. Finally, the virtual absence of antagonistic effect on mediator substances in isolated organs (catecholamines, muscarine-like effect of acetylcholine) militates in favor of the same inactivity toward these neuromodulators in the nerve centers. Furthermore, in isolated organs (ileon of the rabbit) the compound shows antinicotinic and antiamphetaminic properties which would seem to indicate that its antidepressant effect is not due to any central amphetamine-like activity. In addition, the compound has peripheral antihistaminic and antiserotonic effects which, if they also exist at the nerve centers would help to explain its neuropsychopharmacologic effect.

The objective of the above comments is to identify the characteristics of the products of this invention compared with previous antidepressant drugs and they will be illustrated in the following tables in which the results of a clinical study are summarized concerning a series of depressive states, namely, symptomatic depressive states of psychasthemias, neuroses of anguish and obsessional neuroses, paranoid psychoses of the Schizophrenias, psychosomatic disorders occurring during periods of fatigue and overwork and hypochondrial psychoses.

In these tables, dosage is expressed in the number of 50 mg. tablets administered per day. The first table II lists the results obtained in ambulatory patients and the second table III sums up the results obtained in institutionalized patients.

When all these findings are put together they show twelve very positive responses and eight positive responses out of twenty-four patients.

TABLE II

| Ambulatory Patients | Sex | Average Dose | Duration of treatment | Category of Patient | Results Obtained |
|---|---|---|---|---|---|
| 6. M.M. 30 yrs. | F | 2 | 10 | depressive state over work anxiety | +++ |
| 7. N.G 32 yrs. | F | 2 | 8 | fatigue hypochondria obsessive structure | +++ |
| 8. J.O. 48 yrs. | M | 1 | 6 | fatigue due to overwork | + |
| 9. B.G. 45 yrs. | F | 1 | 10 | psychasthenia and obsessive background | +++ |
| 2nd try | | 2 | 21 | | |
| 10. H.O. 49 yrs. | F | ½ | 6 | Reactive depressive state | + |
| 11. Y.O. 14 yrs. | F | ½ | 10 | school fatigue | ++ |
| 12. N.O. 10 yrs | F | ½ | 1 | no disorder | 0 |
| 13. G.M. 37 yrs. | F | ½ | 10 | no disorder | ++ |
| 14. P.M. 30 yrs. | M | 1 | 10 | no disorder | +++ |
| 15. F.G. 43 yrs. | M | 1 | 2 | reactive fatigue | 0 |
| 16. E.D. 47 yrs. | M | 2 | 15 | depressive state due to a previous myocardial infarct - anxiety | +++ |
| 17. C.H. 25 yrs. | M | 3 | 10 | overwork during examinations psychasthenic personality | +++ |
| 18. P.F. 45 yrs. | M | 2 | 10 | depressive state secondary to psychosomatic disorders and intoxication with tobacco | +++ |
| 19. J.M. 26 yrs. | F | 2 | 6 | hysteria neurosis | + |
| 20. R.P. 33 yrs. | M | 1 | 10 | reactive depressive state anxiety agitation anorexia | +++ |
| 21. H.R. 38 yrs. | M | 1 | 10 | no disorder | ++ |

TABLE III

| INSTITUTIONALIZED PATIENTS | Sex | Average Dose | Duration of treatment | Category of Patient | Results Obtained |
|---|---|---|---|---|---|
| 1. E.P. 38yrs. | M | 3 | 30 | psychastenia | +++ |
| 2. P.C. 25 yrs | M | 2 | 8 | psychopathic state triggered by narcotics | 0 |
| 3. F.M. 26 yrs. | F | 2 | 20 | "border-line" type psychoneurosis | +++ |
| 4. A.B. 31 yrs. | M | 2 | 8 | paranoid schizophrenia | + |
| 5. L.H. 32 yrs. | F | 2 | 15 | obsessive phychoneurosis | ++ |
| 22. M.P. 52 yrs. | M | 3 | 2 | melancholia state of | 0 |
| 23. D.R. 41 yrs. | M | 2 | 15 | paranoid psychosis | ++ |
| 24. L.P. 59 yrs. | F | 2 | 10 | involutional depressive state - due to cerebral atherosclerosis | +++ |

TABLE IV

Finally, the following table sums up the symptomatic findings of a clinical trial covering a number of patients.

| Table of the Symptomatic Findings (1) | Number of Cases |
|---|---|
| Increase of intellectual efficiency and better capacity for work. | 16 |
| Clarification of thought and better organization of thought and ideas. | 15 |
| Improvement in memory. | 12 |
| Return of energy - disappearance of fatigue. | 17 |
| Improvement of sexual activity. | 6 |
| Disappearance of psychosomatic disorders. | 10 |
| of anguish and anxiety. | 11 |
| Improvement of sleep disorders. | 4 |
| Improvement of relations with others. | 13 |

(1) The normal nomenclature is not considered here but only the verbal comments of the patients who underwent the clinical trial.

What is claimed is:

1. A method of alleviating depressive states in a patient subject to depression, which comprises administering orally to said patient daily an effective amount of 3-morpholinoethylamino-4-methyl-6-phenylpyridazine or a non-toxic acid addition salt thereof.

2. The method of claim 1 in which the active ingredient is administered with a pharmaceutical carrier in a pharmaceutical composition.

3. The method of claim 2 in which the pharmaceutical composition is in the form of a tablet.

4. The method of claim 1 in which the active ingredient is the dihydrochloride salt.

* * * * *